United States Patent [19]

Platel et al.

[11] Patent Number: 4,639,452

[45] Date of Patent: Jan. 27, 1987

[54] ARYLIC DERIVATIVES OF PIPERAZINE, THE METHOD OF PREPARING SAME AND THEIR APPLICATION IN THERAPEUTICS

[75] Inventors: Alain Y. Platel, Rueil Malmaison; Guy R. Bourgery, Colombes, both of France; Alain Lacour, deceased, late of Saint Maur des Fossés, France, by Hélène Christiane José Guiblain, Cécile Hélène Laurence Lacour, Laurent Pierre Rolland Lacour, heirs

[73] Assignee: Delalande S.A., Courbevoie, France

[21] Appl. No.: 469,968

[22] Filed: Feb. 25, 1983

[30] Foreign Application Priority Data

Feb. 26, 1982 [FR] France .................. 82 03256

[51] Int. Cl.$^4$ .................. C07D 295/18; A61K 31/495
[52] U.S. Cl. .................. 514/252; 544/121; 544/360; 544/365; 544/372; 544/377; 544/386; 544/391; 544/399; 544/400; 514/227; 514/255
[58] Field of Search .............. 544/360, 372, 377, 386, 544/389, 391, 121, 365, 400, 399; 424/250; 514/227, 252, 255

[56] References Cited

U.S. PATENT DOCUMENTS

| | | | |
|---|---|---|---|
| 3,573,291 | 3/1971 | Fauran et al. | 424/250 |
| 3,590,034 | 6/1971 | Fauran et al. | 424/250 |
| 3,634,411 | 1/1972 | Fauran et al. | 424/250 |
| 3,753,984 | 8/1973 | Fauran et al. | 424/250 |
| 4,029,650 | 6/1977 | Raynaud et al. | 544/360 |

FOREIGN PATENT DOCUMENTS

| | | | |
|---|---|---|---|
| 2240734 | 3/1975 | France | 544/372 |
| 1168108 | 10/1969 | United Kingdom | 544/387 |
| 1258726 | 12/1971 | United Kingdom | 544/386 |

Primary Examiner—George F. Lesmes
Assistant Examiner—S. A. Gibson
Attorney, Agent, or Firm—Roylance, Abrams, Berdo & Goodman

[57] ABSTRACT

New derivatives are provided corresponding to the formula:

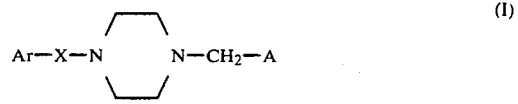

(I)

in which Ar represents an aromatic nucleus; and X represents:
either the trans

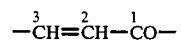

chain or the

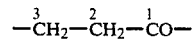

chain and A=CONHOH, COOEt, COOH or $CONR_2R_3$,
either the trans-CH=CH—$CH_2$— chain or —$CH_2$—$CH_2$—$CH_2$ chain and A=carboxamido, N-isopropylcarboxamido, pyrrolidinocarbonyl or piperidinocarbonyl.

These derivatives and their salts are used as drug for their activity stimulating, protecting and/or correcting cerebral functions.

21 Claims, No Drawings

ARYLIC DERIVATIVES OF PIPERAZINE, THE METHOD OF PREPARING SAME AND THEIR APPLICATION IN THERAPEUTICS

The present invention relates to new arylic derivatives of piperazine, their salts and the method or preparing same as well as the application in therapeutics of these derivatives and of these salts.

The new derivatives of the invention correspond more precisely to the general formula:

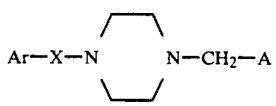

in which X represents: either the chain of trans configuration $$-\overset{3}{C}H=\overset{2}{C}H-\overset{1}{C}O-$$

or the chain $$-\overset{3}{C}H_2-\overset{2}{C}H_2-\overset{1}{C}O-,$$

connected to Ar by their carbon atom 3, in which case A represents:
- a carbohydroxamic (—CONHOH) or hydroxymethyl (—CH$_2$OH) group, Ar then representing the (3,4,5-trimethoxy)phenyl nucleus,
- an ethoxycarbonyl (COOEt) group, Ar then representing the para-fluorophenyl, (3,4-dichloro)phenyl, (2,3,4-trimethoxy)phenyl or (2,4,6-trimethoxy)phenyl nucleus,
- a carboxyl group (COOH), Ar then representing the parachlorophenyl, para-hydroxyphenyl, (3,4-methylenedioxy)phenyl or (3,5-dimethoxy, 4-hydroxy)phenyl nucleus, or
- an amido group of structure CO—NR$_2$R$_3$ in which the pair (R$_2$,R$_3$) takes on one of the following meanings: (H,H), (H, C$_1$-C$_4$ alkyl) (C$_1$-C$_4$ alkyl, C$_1$-C$_4$ alkyl), (H, C$_3$-C$_6$ cycloalkyl), (H, C$_3$-C$_6$ cycloalkylmethyl), (H, phenyl), (H, phenyl substituted by one or more halogen atoms), (H, phenyl substituted by one or more methyl or methoxy groups), (H, benzyl), (H, benzyl substituted by one or more halogen atoms), (H, benzyl substituted by one or more methyl or methoxy groups), (CH$_3$, benzyl), (CH$_3$, benzyl substituted by one or more halogen atoms), (CH$_3$, benzyl substituted by one or more methyl or methoxy groups), (H, allyl), (H, propargyl), R$_2$, R$_3$ being also able to form jointly with the nitrogen atom to which they are linked, a pyrrolidino, piperidino, tropanic

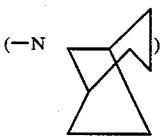

or morpholino radical; Ar then representing a phenyl nucleus, a phenyl nucleus substituted by one or more halogen atoms, by one or more methoxy groups, by a methyl group, by a trifluoromethyl group or by one or two hydroxyl radicals, a 1,3-benzodioxolyl group

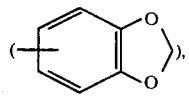

a 1,4-benzodioxannyl group

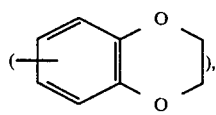

a (5-methoxy) 1,4-benzodioxannyl group

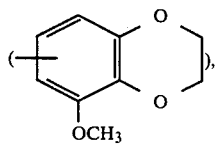

a naphthyl group, the (3-methoxy 4-hydroxy)phenyl group, the (3-hydroxy 4-methoxy)phenyl group, the (3,5-dimethoxy 4-hydroxy)phenyl group or a (4-C$_2$-C$_4$ alkoxy 3,5-dimethoxy)phenyl group;

A not however being able to assume the following values: CONHCH$_3$, CONHC$_2$H$_5$, CONHC$_3$H$_7$n, CONHC$_3$H$_7$iso, CON(CH$_3$)$_2$, CON(C$_2$H$_5$)$_2$, CON(C$_3$H$_7$n)$_2$, CON(C$_3$H$_7$iso)$_2$,

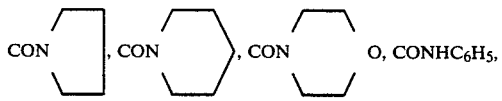

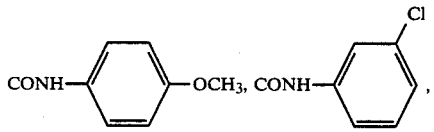

when Ar represents the (3,4,5-trimethoxy)phenyl or (3,5-dimethoxy 4-hydroxy)phenyl group;
or the chain of trans configuration $$-\overset{1}{C}H=\overset{2}{C}H-\overset{3}{C}H_2-,$$

linked to Ar by its carbon atom 1 or the chain —CH$_2$—CH$_2$—CH$_2$—, in which case A represents a carboxamido, N-isopropylcarboxamido, pyrrolidinocarbonyl or piperidinocarbonyl group, Ar then representing a (3,4,5-trimethoxy)phenyl or (3,4-methylenedioxy)phenyl group.

Among the derivatives of formula (I), there may be mentioned as particularly interesting the compounds in which X represents the trans chain $$-\overset{3}{C}H=\overset{2}{C}H-\overset{1}{C}O-$$

and A represents a COOH group or a group of formula CONR$_2$R$_3$ and more especially the group CONH₂ CONH— 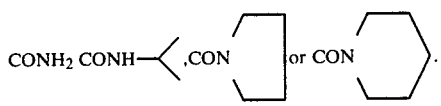

The present invention relates also to the mineral or organic acid (for example hydrochloric acid and maleic or oxalic acid) addition salts of the derivatives of formula (I), as well as the hydrates of said derivatives and salts.

The process of the invention for preparing the compounds of formual (I) in which X represents the chain of trans configuration

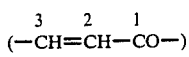

or the chain (—CH₂—CH₂—CO—) and Ar has the same meanings as in formula (I), except the values p-hydroxyphenyl, (4-hydroxy 3-methoxy)phenyl, (4-hydroxy 3,5-dimethoxy)phenyl, (3,4-dihydroxy)phenyl and (3-hydroxy 4-methoxy)phenyl consists:

(A) in the case where A represents an ethoxycarbonyl or amido group of structure

where R₂ and R₃ have the same meanings as in formula (I):
in forming the chloride of the acids or formula:

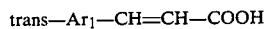 (II)

or

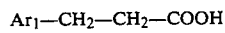 (IIa)

in which Ar₁ has the same meanings as Ar in formula (I), except for the values p-hydroxyphenyl, (4-hydroxy 3-methoxy)phenyl, (4-hydroxy 3,5-dimethoxy)phenyl, (3-hydroxy 4-methoxy)phenyl and (3,4-dihydroxy)phenyl, preferably by action of thionyl chloride, in solution in toluene, benzene, chloroform, methylene chloride or T.H.F. on these acids, then in condensing the intermediate acid chlorides thus obtained, with the appropriate compounds of formula:

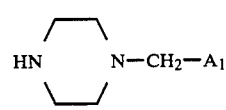 (III)

in which A₁ represents an ethoxycarbonyl or amido group of structure

where R₂ and R₃ have the same meanings as in formula (I), in condensing the acids of formula (II) or (IIa) and the appropriate compounds of formula (III) according to the so-called "BOISSONNAS" reaction, or in treating the acids of formula (II) or (IIa) with the triphenylphosphine-carbon tetrachloride complex, preferably in solution in dioxanne, then condensing the amines of formula (III) on the intermediates obtained;

(B) in the case where A represents an ethoxycarbonyl, carboxyl or amido group of structure CONR₂R₃ where R₂ and R₃ have the same meanings as in formula (I), in condensing the compounds of formula:

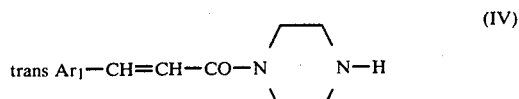 (IV)

or

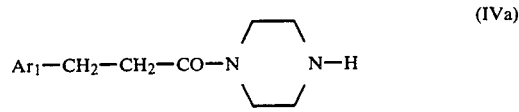 (IVa)

in which Ar₁ has the same meanings as in formula (II) with the appropriate compounds of formula:

 (V)

in which A₂ represents a carboxyl, ethoxycarbonyl or amido group of structure

where R₂ and R₃ have the same meanings as in formula (I), this condensation being preferably carried out in an aprotic medium (acetonitrile, acetone, THF, DMF or toluene for example) and in the presence of potassium carbonate. As for the compounds of formula (IV) and formula (IVa), they are respectively obtained by condensing, in an acetic acid medium, the acid chlorides of formula (II) and formula (IIa) with the piperazine hydrochloride of formula:

 (VI)

(C) in the case where A represents an amido group of structure

where R₂ and R₃ have the same meanings as in formula (I):
either in condensing, by the "BOISSONNAS" method, the acids of formula:

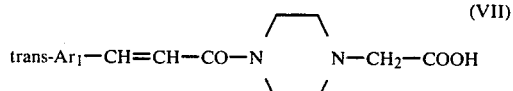

or

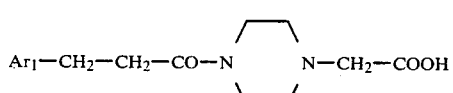

in which Ar₁ has the same meanings as in formula (II) with the appropriate amines of formula:

in which $R_2$ and $R_3$ have the same meanings as in formula (I), the compounds of formula (VII) and (VIIa) being obtained according to the method described in preceding point B, or in condensing the compounds of formula:

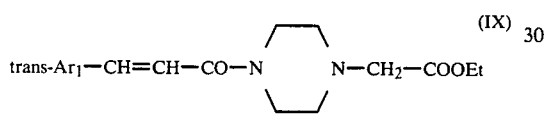

or

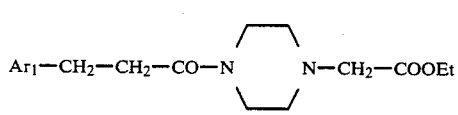

in which Ar₁ has the same meanings as in formula (II), with the appropriate compounds of formula (VIII), in the presence of ammonium chloride, the compounds of formula (IX) or (IXa) being prepared according to the methods described in the preceding points (A) and (B).

The process of the invention for preparing compounds of formula (I) in which X represents the trans

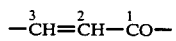

chain or the

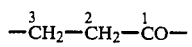

chain, A represents an ethoxycarbonyl or amido group of structure CONR₂R₃ where R₂ or R₃ have the same meanings as in formula (I) and Ar represents a para-hydroxyphenyl, (4-hydroxy 3-methoxy)phenyl, (4-hydroxy 3,5-dimethoxy)phenyl, (3-hydroxy 4-methoxy)phenyl or (3,4-dihydroxy)phenyl nucleus consists in condensing, in the presence of dicyclohexylcarbodiimide (DCCI) and preferably in solution in chloroform, the acids of formula:

or

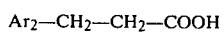

in which Ar₂ represents a 4-hydroxy phenyl, (4-hydroxy 3-methoxy)phenyl, (4-hydroxy 3,5-dimethoxy)phenyl, (3-hydroxy 4-methoxy)phenyl or (3,4-dihydroxy)phenyl nucleus, with the compounds of formula (III).

The process of the invention for preparing the compounds of formula (I) in which X represents the trans

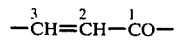

chain or the

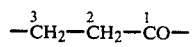

chain, A represents the carboxyl group and Ar represents a 4-hydroxy phenyl or (4-hydroxy 3,5-dimethoxy)-phenyl nucleus consists in hydrolyzing, preferably with aqueous NaOH the compounds of formula (I) having the particular structure:

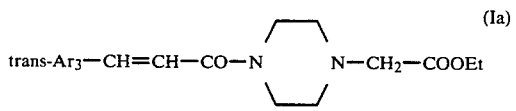

or

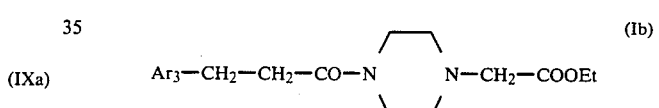

in which Ar₃ represents a parahydroxyphenyl or (4-hydroxy 3,5-dimethoxy)phenyl group.

The compounds of formulae (Ia) and (Ib) are prepared according to the above-described process from the compounds of formula (IIb) or (IIc) and the compounds of formula (III).

The process of the invention for preparing the compounds of formula (I) in which A represents the hydroxymethyl chain consists in condensing the compounds of formula (IV) or (IVa), in which Ar₁ represents (3,4,5-trimethoxy)phenyl nucleus, with ethylene oxide, preferably in solution in ethanol.

The process of the invention for preparing the compounds of formula (I) in which A represents the carbohydroxamic group (—CONHOH) consists in condensing hydroxylamine, preferably in hydrochloride form and in the presence of sodium methylate, on the compounds of formula (I) having the particular structure:

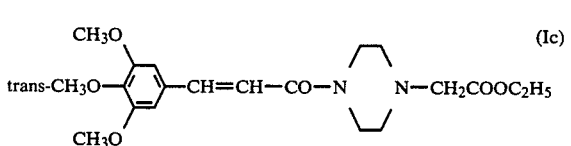

or

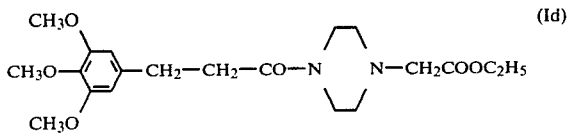 (Id)

The process of the invention for preparing the compounds of formula (I) in which X represents the trans

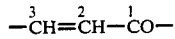

chain consists:
either in condensing the aldehydes of formula:

$$trans-Ar_4-CH=CH-CHO \qquad (X)$$

in which $Ar_4$ represents a (3,4,5-trimethoxy)phenyl or (3,4-methylenedioxy)phenyl group with the compounds of formula (III) in which $Ar_1$ represents a carboxamido, N-isopropylcarboxamido, pyrrolidinocarbonyl or piperidinocarbonyl group, then in reducing the intermediate compounds thus obtained preferably with sodium borohydride in solution in methanol, the compounds (X) being known or prepared according to the technique described in Indian J. Chem. Vol. 13 pages 10–15 (1975);

or in condensing the halogenated derivatives of formula:

$$trans-Ar_4-CH=CH-CH_2-hal. \qquad (XI)$$

in which $Ar_4$ has the same meanings as in formula (X) and hal designates a halogen atom, with the compounds of formula (III) in which $A_1$ represents a carboxamido, N-isopropylcarboxamido, pyrrolidinocarbonyl or piperidinocarbonyl group, preferably in toluene and in the presence of a base such as triethylamine, the compound of formula (XI) being known or prepared in accordance with the technique described in German patent No. 2 252 080.

The process of the invention for preparing the compounds of formula (I) in which X represents the propylene chain ($-CH_2-CH_2-CH_2-$) consists in halogenating the compounds of formula:

$$Ar_4-(CH_2)_3 OH \qquad (XII)$$

in which $Ar_4$ has the same meanings as in formula (X), preferably with phosphorous tribromide, then in causing to react on the intermediate halogenated derivative obtained, the compounds of formula (III) in which $A_1$ represents a carboxamido, N-isopropylcarboxamido, pyrrolidincarbonyl or piperidinocarbonyl group.

The compounds of formula (XII) are known or prepared by reduction with AlLiH$_4$ in THF of the corresponding ethyl cinnamoates, themselves known or prepared according to the technique described in Indian J. Chem. Vol 13, pages 10–15 (1975).

The compounds of formula (I) in which X represents the

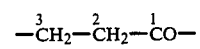

chain, A represents an ethoxycarbonyl group or a group of structure $CONR_2R_3$, where $R_2$ and $R_3$ have the same meanings as in formula (I) and Ar has the same meanings as $Ar_1$ in formula (II), may also be obtained by catalytic reduction, prefarably in the presence of 10% palladium on charcoal and in alcohol medium, of the compounds of formula (I) having the particular structure:

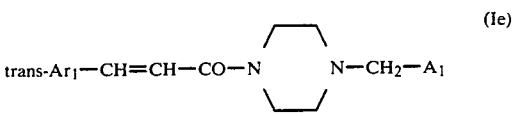 (Ie)

in which $Ar_1$ has the same meanings as in formula (IV) and $A_1$ hs the same meanings as in formula (III).

The derivatives of formula (I) may be salified by the usual methods. Salification may for example be obtained by action on these derivatives of a mineral acid such as hydrochloric acid or an organic acid such as oxalic or maleic acid, this operation being preferably carried out in a solvent or a mixture of solvents such as acetone, ethanol or water.

The following preparations are given by way of example to illustrate the invention.

EXAMPLE 1 trans-1-cinnamoyl 4-pyrrolidinocarbonylmethyl piperazine hydrochloride (I)

Code number: 36

To a solution of 38.5 g of cinnamoyl chloride (trans) in 200 ml of toluene are slowly added, at room temperature, 22.1 g of 4-pyrrolidinocarbonylmethyl piperazine (III). Then it is left under agitation at room temperature for 4 hours, the precipitate is filtered and recrystallized in alcohol. 15 g of the expected compound were thus isolated (Yield ≈42%).

By the same process, but from the corresponding reagents, the compounds of formula (I) were obtained, shown under code numbers 3 to 6, 10 to 16, 18 to 24, 27 to 34, 37 to 57 and 78 to 89 in table I below.

EXAMPLE 2 trans-1-(3,4-methylenedioxy)cinnamoyl 4-pyrrolidinocarbonyl piperazine, hydrochloride (I)

Code number: 37

To a solution cooled to 5° C. of 19.2 g trans(3,4-methylenedioxy)cinnamic acid (II) in 200 ml of dimethylformamide, are added 14 ml of triethylamine, then 9.6 ml of ethyl chloroformiate. It is left at 5° C. for 30 minutes, then 39.4 g of 4-pyrrolidinocarbonylmethyl piperazine (III) are slowly added. Then it is left for 12 hours at room temperature. Thus, 13 g (Yield ≈36%) of the expected product were obtained.

By the same process, but from the corresponding reagents, the compounds of formula (I) were obtained, shown under code numbers 3 to 6, 10 to 16, 18 to 24, 27 to 34, 36 and 38 to 57, in table I.

Similarly, by this process, but from the compounds of formula (VII) or (VIIa) and the amines of formula (VIII), the compounds of formula (I) were obtained; shown under code numbers 10 to 16, 18 to 24, 27 to 34, 36 to 57 and 78 to 89.

EXAMPLE 3 trans-1-(2,4,6-trimethoxy)cinnamoyl 4-N-isopropylaminocarbonylmethyl piperazine, oxalate (I)

Code number: 16

A solution of 26 g of triphenylphosphine in 100 ml of carbon tetrachloride and 300 ml of dioxane is maintained for an hour at 70° C. Then it is cooled to 5°–10° C., 14.9 g of trans(2,4,6-trimethoxy)cinnamic acid are added, it is left for 30 minutes at 5°–10° C., then 55.5 g of 4-N-isopropylaminocarbonylmethyl piperazine (III) are added and the solution is heated at about 70° C. for two hours. Then it is filtered, the filtrate evaporated, the residue is taken up in chloroform, then extracted with a dilute oxalic acid solution, the aqueous phase is washed with ether, neutralized with sodium bicarbonate, the precipitate formed (base-melting point 93° C.) is filtered, dissolved in acetone, an acetonic solution of oxalic acid is added, the precipitate formed filtered and recrystallized in n-butanone. Thus 9 g (Yield ≃36%) of the expected compound are obtained.

By the same process, but from the corresponding reagents, the compounds of formula (I) are obtained shown under code numbers 3 to 6, 10 to 15, 18 to 24, 27 to 34, 36 to 57 and 78 to 89 in table I.

EXAMPLE 4 trans-1-(3,4,5-trimethoxy)cinnamoyl 4-aminocarbonylmethyl piperazine (I)

Code number: 11

A suspension of 15.3 g of trans(3,4,5-trimethoxy)cinnamoylpiperazine (IV), 9.3 g of chloroacetamide and 20.7 g of potassium carbonate in 200 ml of acetonitrile is heated to reflux for 3 hours. Then it is filtered, the filtrate evaporated and the residue recrystallized in ethanol. Thus, 13 g (Yield ≃72%) of the expected compound are obtained.

By the same process, but from the corresponding reagents, the compounds of formula (I) are obtained which are shown in table I under code numbers 3 to 10, 12 to 16, 18 to 24, 27 to 34, 36 to 57 and 78 to 89.

EXAMPLE 5 trans-1-(3,4,5-trimethoxy)cinnamoyl 4-N-cyclopentylaminocarbonylmethyl piperazine (I)

Code number: 23

A mixture of 19.6 g of 1-(3,4,5-trimethoxy)cinnamoyl 4-ethoxycarbonylmethyl piperazine trans (IX), 42 g of cyclopentylamine (VIII) and 2 g of ammonium chloride is heated to 90°–100° C. for 7 hours. Then the excess amine is evaporated in a vacuum and the residue is taken up in water, extracted with chloroform, washed with water, dried on sodium sulfate, filtered and the filtrate evaporated. The product obtained in crystallized in ether and recrystallized in ethyl acetate, then in isopropylic alcohol. Thus, 2.6 g of the expected compound are obtained (Yield ≃12%).

By the same process, but from the corresponding reagents, the compounds of formula (I) are obtained which are shown in table I under code number 10 to 16, 18 to 24, 27 to 34, 36 to 57 and 78 to 89.

EXAMPLE 6 trans-1-(4-hydroxy 3-methoxy)cinnamoyl 4-N-isopropylaminocarbonylmethyl piperazine (I)

Code number: 26

To a solution, cooled to 0° C., of 9.7 g of trans(4-hydroxy 3-methoxy)cinnamic acid (IIb) and 9.2 g of N-isopropylaminocarbonylmethyl piperazine (III) in 250 ml of dioxanne are added 10.3 g of DCCI. Then it is left at room temperature for 70 hours, filtered, the filtrate is evaporated and the residue chromatographed on a silica column. By eluting with the methylene chloride (95%)—methanol (5%) mixture, 6 g (Yield ≃33%) of the expected product are obtained which is recrystallized in isopropylic ether.

By the same process, but from the corresponding reagents, the compounds of formula (I) shown in table I under code numbers 25 and 74 to 77 are obtained, as well as the compound of formula (Ia): trans-1-parahydroxycinnamoyl 4-ethoxycarbonylmethyl piperazine, hydrochloride whose characteristics are the following:

Melting point: 248° C.
Empirical formula: $C_{17}H_{23}ClN_2O_4$
Molecular weight: 354.83
Elementary analysis:

|  | C | H | N |
| --- | --- | --- | --- |
| Calculated (%) | 57.54 | 6.53 | 7.90 |
| Obtained (%) | 57.12 | 6.66 | 7.86 |

EXAMPLE 7 trans-2-[4-(1-(4-hydroxy)cinnamoyl)piperazinyl]acetic acid (I)

Code number: 8

A solution of 3.5 g of 1-parahydroxycinnamoyl 4-ethoxycarbonylmethyl piperazine (Ia) in 30 ml of 1N aqueous NaOH is heated at 60° C. for 90 minutes, then it is acidified to pH 6-5 with 1N aqueous hydrochloric acid, the precipitate obtained is filtered and washed on the filter with ethanol. Thus, 1.6 g (Yield ≃55%) of the expected product is obtained.

EXAMPLE 8 trans-1-(3,4,5-trimethoxy)cinnamoyl 4-(2-hydroxy)ethyl piperazine maleate (I)

Code number: 2

A solution of 15 g of trans-(3,4,5-trimethoxy)cinnamoyl piperazine (IV) and 2 ml of piperidine in 40 ml of alcohol is heated to 60° C. Then an ethylene oxide gas stream is passed therethrough (until 0.05 mole has been absorbed) and it is left at 60° C. for 1 hour, then at room temperature for 12 hours. Then it is evaporated and the residue chromatographed on a silica column. It is eluted with a methylene chloride (95%)—methanol (5%) mixture and the pure product obtained is dissolved in acetone. An acetonic solution of maleic acid is added and the formed precipitate is filtered. Thus, the expected product was isolated with a yield of 76%.

EXAMPLE 9 trans-[4-(3,4,5-trimethoxy cinnamoyl)piperazine-1-yl]acethydroxamic acid (I)

Code number: 1

To a solution, cooled to 5° C., of 13.8 g of sodium in 300 ml of methanol is added a solution of 20.8 g of hydroxylamine hydrochloride in 200 ml of methanol. It is filtered and to the filtrate, at room temperature, are added 68.8 g of ethylic ester of [4-(3,4,5-trimethoxy cinnamoyl)piperazine-1-yl]acetic acid (trans). After 20 hours of reaction, the solvent is evaporated, the residue is taken up in water, washed with ether, then a solution of 18 g of acetic acid in 30 ml of water is added. The precipitate obtained is filtered, washed with water, dried in a vacuum and recrystallized in 280 ml of acetone at 70%. 37 g of the expected product are isolated (Yield ≃47%).

EXAMPLE 10 trans-1-(3,4,5-trimethoxy)cinnamyl 4-N-isopropylaminocarbonyl methyl piperazine (I)

Code number: 58

A mixture of 8.8 g of trans(3,4,5-trimethoxy)cinnamaldehyde (X) and 7.4 g of 4-N-isopropylaminocarbonylmethyl piperazine (III) in 300 ml of methanol is heated at 40° C. for 1 hour, then 6 g of sodium borohydride are slowly added. After an hour, the solvent is evaporated, the residue is taken up in chloroform, washed with water, dried on sodium sulfate, filtered and the filtrate evaporated. The product obtained is recrystallized in isopropylic ether then in ethyl acetate. Thus, 2 g (Yield ≃16%) of the expected product are obtained.

EXAMPLE 11 trans-1-(3,4-methylenedioxy)cinnamyl 4-pyrrolidinocarbonylmethyl piperazine, hydrochloride (I)

Code number: 61

To a solution of 2.6 g of 4-pyrrolidinocarbonylmethyl piperazine (III) in 16 ml of toluene and 0.9 ml of triethylamine is slowly added at room temperature, 1.6 g of trans-3-(3,4-methylenedioxy)phenyl 1-bromo prop-2-ene (XI). Then it is left at room temperature for 12 hours, filtered, the filtrate is evaporated and the residue crystallized in ether. 1.5 g (Yield ~65%) of a product is obtained which corresponds to the expected product in base form (melting point 110° C.). This product is then dissolved in ethanol, a solution of hydrochloric acid ≃6.5N in ethanol is added and the precipitate obtained is filtered which corresponds to the expected product.

EXAMPLE 12

1-[3-(3,4,5-trimethoxy)phenyl propyl]4-N-isopropylaminocarbonyl methyl piperazine, dioxalate (I)

Code number: 62

To a solution of 24 g of 3-(3,4,5-trimethoxy)phenyl propan-1-ol (XII) in 200 ml of chloroform are slowly added 57.2 g of phosphorous tribromide ($PBr_3$). Then it is left under agitation at room temperature for 1 hour, it is diluted with water, the organic phase is decanted, it is washed with a saturated solution of sodium bicarbonate, dried on sodium sulfate, filtered and the filtrate evaporated. The residue is crystallized in petroleum ether and dissolved in 150 ml of acetonitrile. 13.8 g of potassium carbonate and 6.8 g of 4-N-isopropylaminocarbonylmethyl piperazine (III) are added and the mixture is heated at reflux for 7 hours. Then the insoluble matter is filtered, the filtrate is evaporated, the residue is dissolved in chloroform, washed with water, dried on sodium sulfate, filtered, the filtrate is evaporated, the residue is dissolved in ethanol, an ethanol solution of oxalic acid is added, the precipitate obtained is filtered and recrystallized in absolute alcohol. Thus, 4 g (Yield ~20%) of the expected product is isolated.

The compound of formula (I) shown under code number 63 in table I may also be prepared by using the same process, but from the corresponding reagents.

EXAMPLE 13

3-(3,4,5-trimethoxy)phenyl 1-[4-(N-3,4,5-trimethoxy)benzylamino carbonylmethyl piperazine-1-yl]propanone (I)

Code number: 57

A suspension of 6 g of compound (I) of code number 29 and 1 g of 10% palladium on charcoal in 500 ml of ethanol is heated for 5 hours 30 minutes at 50° C. under a hydrogen pressure. Then it is filtered and the filtrate is evaporated. The residue is chromatographed on a silica column. By eluting with a methylene chloride (90%)—methanol (10%) mixture, 5.4 g of the expected product are isolated (Yield ≃90%).

TABLE I $$Ar-X-N\underset{}{\overset{}{\bigcirc}}N-CH_2-A \qquad (I)$$

| Code Number | Ar— | —X— | A— | Form | Empirical Formula | Molecular weight | Melting point (°C.) | % | ELEMENTARY ANALYSIS C | H | N |
|---|---|---|---|---|---|---|---|---|---|---|---|
| 1 | 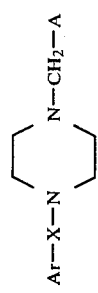 CH₃O, CH₃O, CH₃O | —CH=CH—CO— (trans) | —CONHOH | Base | C₁₈H₂₅N₃O₆ | 379.40 | 134 | Cal. Obt. | — — | — — | — — |
| 2 | " | —CH=CH—CO— (trans) | —CH₂OH | Maleate | C₂₂H₃₀N₂O₉ | 466.48 | 159 | Cal. Obt. | 56.64 56.35 | 6.48 6.43 | 6.01 6.16 |
| 3 | F-⌬- | —CH=CH—CO— (trans) | —COOEt | HCl | C₁₇H₂₂ClFN₂O₃ | 356.82 | 205 | Cal. Obt. | 57.22 57.19 | 6.21 6.23 | 7.85 7.93 |
| 4 | Cl, Cl-⌬- | —CH=CH—CO— (trans) | " | Base | C₁₇H₂₀Cl₂N₂O₃ | 371.26 | 92 | Cal. Obt. | 54.99 54.79 | 5.43 5.41 | 7.55 7.69 |
| 5 | CH₃O, CH₃O, CH₃O (1,2,3) | —CH=CH—CO— (trans) | " | Maleate | C₂₄H₃₂N₂O₁₀ | 508.51 | 127 | Cal. Obt. | 56.68 56.59 | 6.34 6.40 | 5.51 5.53 |
| 6 | CH₃O, CH₃O, CH₃O (3,4,5) | —CH=CH—CO— (trans) | " | Oxalate | C₂₂H₃₀N₂O₁₀ | 482.48 | 177 | Cal. Obt. | 54.76 54.36 | 6.27 6.30 | 5.81 5.75 |

TABLE I-continued $$Ar-X-N\underset{\phantom{XX}}{\overset{\phantom{XX}}{\bigcirc}}N-CH_2-A \quad (I)$$

| Code Number | Ar— | —X— | A— | Form | Empirical Formula | Molecular weight | Melting point (°C.) | | % | ELEMENTARY ANALYSIS C | H | N |
|---|---|---|---|---|---|---|---|---|---|---|---|---|
| 7 | 4-Cl-C₆H₄— | —CH=CH—CO— (trans) | —COOH | Base + 1.8 H₂O | $C_{15}H_{17}ClN_2O_3$ + 1.8 H₂O | 314.42 | 176 | Cal. Obt. | | 57.30 56.88 | 5.65 6.34 | 8.91 8.85 |
| 8 | 4-HO-C₆H₄— | —CH=CH—CO— (trans) | " | Base + 5.4% H₂O | $C_{15}H_{18}N_2O_4$ + 5.4% H₂O | 306.91 | >260 | Cal. Obt. | | 58.69 59.04 | 6.51 6.62 | 9.13 9.07 |
| 9 | 3,4-methylenedioxyphenyl | —CH=CH—CO— (trans) | " | Base + 1.4% H₂O | $C_{16}H_{18}N_2O_5$ + 1.4% H₂O | 322.84 | 186 | Cal. Obt. | | 59.52 59.41 | 5.78 6.06 | 8.68 8.59 |
| 10 | 4-Cl-C₆H₄— | —CH=CH—CO— (trans) | —CONH₂ | HCl | $C_{15}H_{19}Cl_2N_3O_2$ | 344.24 | 253 | Cal. Obt. | | 52.33 52.08 | 5.56 5.54 | 12.21 12.22 |
| 11 | 3,4,5-tri-CH₃O-C₆H₂— | —CH=CH—CO— (trans) | " | Base | $C_{18}H_{25}N_3O_5$ | 363.40 | 202 | Cal. Obt. | | 59.49 59.35 | 6.92 6.82 | 11.56 11.70 |
| 12 | 3,4-methylenedioxyphenyl | —CH=CH—CO— (trans) | " | HCl + 3.7% H₂O | $C_{16}H_{20}ClN_3O_4$ + 3.7% H₂O | 367.39 | 195 | Cal. Obt. | | 52.30 52.48 | 5.90 6.03 | 11.44 11.76 |

TABLE I-continued $$Ar-X-N\underset{}{\underbrace{\qquad}}N-CH_2-A \qquad (I)$$

| Code Number | Ar— | —X— | A— | Form | Empirical Formula | Molecular weight | Melting point (°C.) | % | ELEMENTARY ANALYSIS C | H | N |
|---|---|---|---|---|---|---|---|---|---|---|---|
| 13 | " | —CH=CH—CO— (trans) | —CON(CH$_3$)(CH$_3$) | HCl | C$_{18}$H$_{24}$ClN$_3$O$_4$ | 381.85 | 254 | Cal. Obt. | 56.61 56.41 | 6.34 6.54 | 11.01 10.94 |
| 14 | (naphthyl) | —CH=CH—CO— (trans) | —CONH—CH(CH$_3$)$_2$ | Base | C$_{22}$H$_{27}$N$_3$O$_2$ | 365.46 | 140 | Cal. Obt. | 72.30 72.36 | 7.45 7.33 | 11.50 11.71 |
| 15 | 2,3,4-(CH$_3$O)$_3$-phenyl | —CH=CH—CO— (trans) | " | Oxalate | C$_{23}$H$_{33}$N$_3$O$_9$ | 495.51 | 170 | Cal. Obt. | 55.75 55.76 | 6.71 6.90 | 8.48 8.63 |
| 16 | 2,4,6-(CH$_3$O)$_3$-phenyl | " | " | " | " | " | 191 | Cal. Obt. | 55.75 55.46 | 6.71 6.40 | 8.48 8.55 |
| 18 | phenyl | —CH=CH—CO— (trans) | —CO—NH—CH(CH$_3$)$_2$ | HCl | C$_{18}$H$_{26}$ClN$_3$O$_2$ | 351.87 | >260 | Cal. Obt. | 61.44 61.43 | 7.45 7.37 | 11.94 11.92 |
| 19 | methylenedioxyphenyl | —CH=CH—CO— (trans) | " | Oxalate + 3/5 H$_2$O | C$_{21}$H$_{27}$N$_3$O$_8$ + 3/5 H$_2$O | 460.26 | 188 | Cal. Obt. | 54.80 55.24 | 6.18 6.54 | 9.13 8.89 |

TABLE I-continued $$Ar-X-N\underset{\diagdown}{\overset{\diagup}{\bigcirc}}N-CH_2-A \qquad (I)$$

| Code Number | Ar— | —X— | A— | Form | Empirical Formula | Molecular weight | Melting point (°C.) | | % | ELEMENTARY ANALYSIS C | H | N |
|---|---|---|---|---|---|---|---|---|---|---|---|---|
| 20 |  CH$_3$O–, CH$_3$O–, CH$_3$O– (3,4,5-trimethoxyphenyl) | —CH=CH—CO— (trans) | —CONH— (t-Bu) | Base | C$_{22}$H$_{33}$N$_3$O$_5$ | 419.51 | 188 | Cal. Obt. | | 62.98 63.17 | 7.93 7.88 | 10.02 10.25 |
| 21 | " | " | —CONHC$_4$H$_{9n}$ | " | C$_{22}$H$_{33}$N$_3$O$_5$ | 419.51 | 148 | Cal. Obt. | | 62.98 62.94 | 7.93 8.16 | 10.02 10.10 |
| 22 | " | " | —CONH—CH$_2$—CH(CH$_3$)$_2$ | " | C$_{22}$H$_{33}$N$_3$O$_5$ | " | 156 | Cal. Obt. | | 62.98 63.20 | 7.93 8.01 | 10.02 9.76 |
| 23 | " | " | —CONH—(cyclopentyl) | " | C$_{23}$H$_{33}$N$_3$O$_5$ | 431.52 | 163 | Cal. Obt. | | 64.01 64.10 | 7.71 7.82 | 9.74 9.79 |
| 24 | " | " | —CONH—(cyclohexyl) | " | C$_{24}$H$_{35}$N$_3$O$_5$ | 445.54 | 138 | Cal. Obt. | | 64.69 64.41 | 7.92 7.85 | 9.43 9.16 |
| 25 | 4-HO-phenyl | —CH=CH—CO— (trans) | —CONH—CH(CH$_3$)$_2$ | HCl + 1.4% H$_2$O | C$_{18}$H$_{26}$ClN$_3$O$_3$ + 1.4% H$_2$O | 372.94 | 244 | Cal. Obt. | | 57.97 58.18 | 7.17 7.54 | 11.26 11.19 |
| 26 | 2-CH$_3$O-4-HO-phenyl | —CH=CH—CO— (trans) | " | Base | C$_{19}$H$_{27}$N$_3$O$_4$ | 361.43 | 159 | Cal. Obt. | | 63.14 62.94 | 7.53 7.84 | 11.63 11.93 |

TABLE I-continued $$Ar-X-N\underset{}{\overset{}{\bigcirc}}N-CH_2-A \quad (I)$$

| Code Number | Ar— | —X— | A— | Form | Empirical Formula | Molecular weight | Melting point (°C.) | | ELEMENTARY ANALYSIS % | | | |
|---|---|---|---|---|---|---|---|---|---|---|---|---|
| | | | | | | | | | | C | H | N |
| 27 | 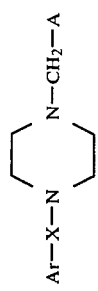 | —CH=CH—CO— (trans) | —CONH—CH₂—CH=CH₂ | " | C₂₁H₂₉N₃O₅ | 403.47 | 155 | Cal. Obt. | | 62.51 62.27 | 7.25 7.20 | 10.42 10.42 |
| 28 | " | —CH=CH—CO— (trans) | —CONH—CH₂—C≡CH | " | C₂₁H₂₇N₃O₅ | 401.45 | 161 | Cal. Obt. | | 62.82 62.45 | 6.78 6.37 | 10.47 10.42 |
| 29 | " | —CH=CH—CO— (trans) | —CONH—CH₂—(3,4,5-trimethoxyphenyl) | " | C₂₈H₃₇N₃O₈ | 543.60 | 174 | Cal. Obt. | | 61.86 61.73 | 6.86 7.04 | 7.73 7.75 |
| 30 | " | —CH=CH—CO— (trans) | —CONH—(2,6-dimethylphenyl) | " | C₂₆H₃₃N₃O₅ | 467.55 | 200 | Cal. Obt. | | 66.79 66.58 | 7.11 7.04 | 8.09 8.84 |
| 31 | " | —CH=CH—CO— (trans) | —CONH—(2,6-dichlorophenyl) | " | C₂₆H₂₉Cl₂N₃O₅ | 598.43 | >250 | Cal. Obt. | | 52.17 52.09 | 4.88 4.92 | 7.02 7.13 |

TABLE I-continued $$Ar-X-N\underset{}{\overset{}{\bigcirc}}N-CH_2-A \quad (I)$$

| Code Number | Ar— | —X— | A— | Form | Empirical Formula | Molecular weight | Melting point (°C.) | ELEMENTARY ANALYSIS % | C | H | N |
|---|---|---|---|---|---|---|---|---|---|---|---|
| 32 | 2,3,4-tri-CH₃O-phenyl | —CH=CH—CO— (trans) | —CO-N(pyrrolidine) | Maleate | $C_{25}H_{35}N_3O_9$ | 533.56 | 109 | Cal. Obt. | 58.52 58.40 | 6.61 6.74 | 7.88 7.99 |
| 33 | 2,4,6-tri-CH₃O-phenyl | —CH=CH—CO— (trans) | " | 1.5 Oxalate | $C_{25}H_{34}N_3O_{11}$ | 552.55 | 200 | Cal. Obt. | 54.34 54.25 | 6.20 6.25 | 7.60 7.63 |
| 34 | " | —CH=CH—CO— (trans) | —CO-N(piperidine) | " | $C_{26}H_{36}N_3O_{11}$ | 566.57 | 218 | Cal. Obt. | 55.11 55.22 | 6.63 6.40 | 7.34 7.42 |
| 36 | phenyl | —CH=CH—CO— (trans) | —CO-N(pyrrolidine) | HCl | $C_{19}H_{26}ClN_3O_2$ | 363.88 | >260 | Cal. Obt. | 62.71 62.57 | 7.20 7.59 | 11.55 11.53 |
| 37 | 3,4-methylenedioxyphenyl | —CH=CH—CO— (trans) | " | " | $C_{20}H_{26}ClN_3O_4$ | 407.86 | >260 | Cal. Obt. | 58.89 58.63 | 6.43 6.16 | 10.30 10.50 |
| 38 | 4-F-phenyl | —CH=CH—CO— (trans) | " | Oxalate | $C_{21}H_{26}FN_3O_6$ | 435.44 | 156 | Cal. Obt. | 57.92 57.52 | 6.02 6.00 | 9.65 9.52 |

TABLE I-continued $$Ar-X-N\underset{\phantom{xx}}{\overbrace{\phantom{xxxxxx}}}N-CH_2-A \qquad (I)$$

| Code Number | Ar— | —X— | A— | Form | Empirical Formula | Molecular weight | Melting point (°C.) | % | ELEMENTARY ANALYSIS C | H | N |
|---|---|---|---|---|---|---|---|---|---|---|---|
| 39 | CH₃O-C₆H₃-OCH₃ (3,4-dimethoxyphenyl) | —CH=CH—CO— (trans) | " | Base + ¼ H₂O | C₂₁H₂₉N₃O₄ + ¼ H₂O | 391.97 | 176 | Cal. Obt. | 64.34 64.60 | 7.59 7.64 | 10.72 10.84 |
| 40 | 3,4-dichlorophenyl | —CH=CH—CO— (trans) | " | HCl | C₁₉H₂₄Cl₂N₃O₂ | 432.78 | >260 | Cal. Obt. | 52.73 52.46 | 5.59 5.47 | 9.71 9.44 |
| 41 | 3-CF₃-phenyl | —CH=CH—CO— (trans) | " | " | C₂₀H₂₅ClF₃N₃O₂ | 431.88 | >260 | Cal. Obt. | 55.62 55.41 | 5.83 5.88 | 9.73 9.64 |
| 42 | 3,4-methylenedioxyphenyl | —CH=CH—CO— (trans) | " | HCl + ¼ H₂O | C₂₁H₂₈ClN₃O₄ + ¼ H₂O | 427.92 | 236 | Cal. Obt. | 58.94 59.16 | 6.75 6.66 | 9.82 9.82 |
| 43 | 3,5-dimethoxyphenyl | —CH=CH—CO— (trans) | " | 1.5 Oxalated + 1/5 H₂O | C₂₄H₃₂N₃O₁₀ + 1/5 H₂O | 526.12 | 188 | Cal. Obt. | 54.79 54.79 | 6.21 6.00 | 7.99 7.70 |
| 44 | 2,3-dimethoxyphenyl | —CH=CH—CO— (trans) | " | Oxalate + 2/5 H₂O | C₂₃H₃₁N₃O₈ + 2/5 H₂O | 484.71 | 193 | Cal. Obt. | 56.99 56.78 | 6.61 6.53 | 8.67 8.52 |

TABLE I-continued $$Ar-X-N\underset{}{\overset{}{\diagdown}}N-CH_2-A \quad (I)$$

| Code Number | Ar— | —X— | A— | Form | Empirical Formula | Molecular weight | Melting point (°C.) | | ELEMENTARY ANALYSIS % | C | H | N |
|---|---|---|---|---|---|---|---|---|---|---|---|---|
| 45 |  | —CH=CH—CO— (trans) | " | 5/4 Oxalate + 1/5 H₂O | C₂₀H₂₇N₃O₂ + 5/4 C₂H₂O₄ + 1/5 H₂O | 457.49 | 202 | Cal. Obt. | | 59.05 58.94 | 6.59 7.05 | 9.18 8.65 |
| 46 | 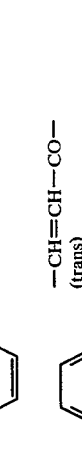 | —CH=CH—CO— (trans) | " | HCl | C₂₀H₂₈ClN₃O₂ | 377.90 | >260 | Cal. Obt. | | 63.56 63.61 | 7.47 7.71 | 11.12 11.24 |
| 47 |  | —CH=CH—CO— (trans) | " | " | C₁₉H₂₅Cl₂N₃O₂ | 398.33 | >260 | Cal. Obt. | | 57.29 57.37 | 6.33 6.47 | 10.55 10.35 |
| 48 |  | —CH=CH—CO— (trans) | " | Oxalate + 2/5 H₂O | C₂₂H₂₉N₃O₇ + 2/5 H₂O | 454.68 | 193 | Cal. Obt. | | 58.11 58.13 | 6.61 6.58 | 9.24 8.62 |
| 49 |  | —CH=CH—CO— (trans) | " | HCl + ¼ H₂O | C₂₁H₃₀ClN₃O₄ + ¼ H₂O | 428.43 | 240 | Cal. Obt. | | 58.81 58.85 | 7.18 7.03 | 9.81 9.85 |
| 50 |  | —CH=CH—CO— (trans) | " | Oxalate + ¼ H₂O | C₂₁H₂₆ClN₃O₆ + ¼ H₂O | 456.40 | 120 | Cal. Obt. | | 55.26 55.23 | 5.85 6.15 | 9.21 9.04 |

TABLE I-continued $$Ar-X-N\underset{}{\overset{}{\bigcirc}}N-CH_2-A \quad (I)$$

| Code Number | Ar— | —X— | A— | Form | Empirical Formula | Molecular weight | Melting point (°C.) | ELEMENTARY ANALYSIS % | | C | H | N |
|---|---|---|---|---|---|---|---|---|---|---|---|---|
| 51 | 3,5-(CH₃O)₂, 4-EtO-phenyl | —CH=CH—CO— (trans) | " | HCl + 1/6 H₂O | C₂₃H₃₄ClN₃O₅ + 1/6 H₂O | 496.81 | 230 | Cal. Obt. | | 55.60 55.95 | 7.55 7.20 | 8.46 8.75 |
| 52 | 4-CH₃O-phenyl | —CH=CH—CO— (trans) | " | HCl + 1/5 H₂O | C₂₀H₂₈ClN₃O₃ + 1/5 H₂O | 397.51 | 249 | Cal. Obt. | | 60.43 60.18 | 7.20 7.16 | 10.57 10.59 |
| 53 | 3-CH₃O, 4,5-OCH₂CH₂O-phenyl | —CH=CH—CO— (trans) | " | Oxalate + ¾ H₂O | C₂₄H₃₁N₃O₉ + ¾ H₂O | 519.02 | 245 | Cal. Obt. | | 55.54 55.78 | 6.31 6.01 | 8.10 8.03 |
| 54 | 3,5-(CH₃O)₂, 4-iPrO-phenyl | —CH=CH—CO— (trans) | " | 1.4 HCl + 4/10 H₂O | C₂₄H₃₅N₃O₅ + 1.4 HCl + 4/10 H₂O | 503.80 | 218 | Cal. Obt. | | 57.21 56.94 | 7.44 7.48 | 8.34 8.65 |
| 55 | 3,4-methylenedioxy-phenyl | —CH=CH—CO— (trans) | —CON⟨piperidine⟩ | HCl | C₂₁H₂₈ClN₃O₄ | 421.91 | 250 | Cal. Obt. | | 59.78 59.36 | 6.69 7.03 | 9.96 9.97 |

TABLE I-continued $$Ar-X-N\underset{\underset{}{\bigcirc}}{\phantom{N}}N-CH_2-A \quad (I)$$

| Code Number | Ar— | —X— | A— | Form | Empirical Formula | Molecular weight | Melting point (°C.) | | ELEMENTARY ANALYSIS | | | |
|---|---|---|---|---|---|---|---|---|---|---|---|---|
| | | | | | | | | % | | C | H | N |
| 56 | 4-Cl-C₆H₄— | —CH=CH—CO— (trans) | " | " | C₂₀H₂₇Cl₂N₃O₂ | 412.35 | 254 | Cal. Obt. | | 58.25 58.04 | 6.60 6.75 | 10.19 10.23 |
| 57 | 3,4,5-(CH₃O)₃-C₆H₂— | —CH₂CH₂—CO— | —CONH—CH₂-(3,4,5-(OCH₃)₃C₆H₂) | Base | C₂₈H₃₉N₃O₈ | 545.62 | 159 | Cal. Obt. | | 61.63 61.40 | 7.21 7.31 | 7.70 7.39 |
| 58 | " | —CH=CH—CH₂— (trans) | —CONH—CH(CH₃)₂ | " | C₂₁H₃₃N₃O₄ | 391.49 | 130 | Cal. Obt. | | 64.62 64.18 | 8.50 8.69 | 10.73 10.54 |
| 59 | " | —CH=CH—CH₂— (trans) | —CON(pyrrolidine) | dioxalate | C₂₄H₃₅N₃O₈ | 583.58 | 240 | Cal. Obt. | | 53.51 53.26 | 6.39 6.46 | 7.20 7.11 |
| 60 | " | —CH=CH—CH₂— (trans) | —CON(piperidine) | 2.2 oxalate | C₂₃H₃₅N₃O₄ + 2.2 (C₂H₂O₄) | 615.61 | 188 | Cal. Obt. | | 53.45 53.42 | 6.45 6.83 | 6.83 6.78 |
| 61 | 3,4-methylenedioxyphenyl | —CH=CH—CH₂— (trans) | —CON(pyrrolidine) | 1.35 HCl + 2.7% H₂O | C₂₀H₂₇N₃O₃ + 1.35 HCl + 2.7% H₂O | 417.80 | 207 | Cal. Obt. | | 57.49 57.38 | 7.14 7.00 | 10.06 10.13 |

TABLE I-continued $$Ar-X-N\underset{\underset{}{\diagdown}}{\overset{\overset{}{\diagup}}{N}}-CH_2-A \quad (I)$$

| Code Number | Ar— | —X— | A— | Form | Empirical Formula | Molecular weight | Melting point (°C.) | % | ELEMENTARY ANALYSIS C | H | N |
|---|---|---|---|---|---|---|---|---|---|---|---|
| 62 | 3,4,5-tri(CH₃O)-C₆H₂ | —(CH₂)₃— | —CONH—CH(iPr) | dioxalate + ½ H₂O | C₂₅H₃₉N₃O₁₂ + ½ H₂O | 582.59 | 188 | Cal. Obt. | 51.54 51.34 | 6.92 6.76 | 7.21 7.04 |
| 63 | " | " | —CON(piperidine) | dioxalate | C₂₆H₃₉N₃O₁₂ | 585.59 | 260 | Cal. Obt. | 53.32 52.95 | 6.71 6.68 | 7.18 7.17 |
| 74 | 4-HO-C₆H₄ | —CH=CH—CO— (trans) | —CON(pyrrolidine) | Oxalate | C₂₁H₂₇N₃O₇ | 433.45 | ≃200 (decomposition) | Cal. Obt. | 58.19 58.19 | 6.28 6.45 | 9.70 9.71 |
| 75 | 3,4-di(HO)-C₆H₃ | —CH=CH—CO— (trans) | " | " | C₂₁H₂₇N₃O₈ | 449.45 | ≃200 (decomposition) | Cal. Obt. | 56.12 55.86 | 6.06 6.28 | 9.35 9.28 |
| 76 | 4-HO-C₆H₄ | —CH=CH—CO— (trans) | —CON(piperidine) | " | C₂₂H₂₉N₃O₇ | 447.48 | 227 | Cal. Obt. | 59.05 59.11 | 6.53 6.75 | 9.39 9.50 |
| 77 | 3,4-di(HO)-C₆H₃ | —CH=CH—CO— (trans) | " | " | C₂₂H₂₉N₃O₈ | 463.48 | 195 | Cal. Obt. | 57.01 57.20 | 6.31 6.59 | 9.07 9.13 |

TABLE I-continued $$Ar-X-N\diagdown N-CH_2-A \quad (I)$$

| Code Number | Ar— | —X— | A— | Form | Empirical Formula | Molecular weight | Melting point (°C.) | | ELEMENTARY ANALYSIS | | |
|---|---|---|---|---|---|---|---|---|---|---|---|
| | | | | | | | | % | C | H | N |
| 78 | 2-OCH₃-C₆H₄ (with CH₃) | —CH=CH—CO— (trans) | " | Base | C₂₂H₂₉N₃O₃ | 371.47 | 127 | Cal. Obt. | 67.90 67.92 | 7.87 7.95 | 11.31 11.43 |
| 79 | 3-CH₃O-C₆H₄ | —CH=CH—CO— (trans) | " | HCl + 4.3% H₂O | C₂₁H₃₀ClN₃O₃ + 4.3% H₂O | 426.30 | 220 | Cal. Obt. | 59.17 59.21 | 7.57 7.31 | 9.86 9.84 |
| 80 | 4-CH₃O-C₆H₄ (with CH₃) | —CH=CH—CO— (trans) | " | HCl | C₂₁H₃₀ClN₃O₃ | 407.93 | 210 | Cal. Obt. | 61.83 61.65 | 7.41 7.47 | 10.30 10.30 |
| 81 | 2-CH₃O,4-CH₃O-C₆H₃ (with CH₃) | —CH=CH—CO— (trans) | " | Base | C₂₂H₃₁N₃O₄ | 401.49 | 106 | Cal. Obt. | 65.81 65.68 | 7.78 7.63 | 10.47 10.34 |
| 82 | 2-OCH₃,4-CH₃O-C₆H₃ (with CH₃) | —CH=CH—CO— (trans) | " | " | C₂₂H₃₁N₃O₄ | 401.49 | 119 | Cal. Obt. | 65.81 65.57 | 7.78 7.51 | 10.47 10.58 |
| 83 | 2,3-di-CH₃O-C₆H₃ (with CH₃) | —CH=CH—CO— (trans) | " | 1.5 Oxalate | C₂₂H₃₁N₃O₄(base) + 1.5 oxalate (C₂₅H₃₄N₃O₁₀) | 536.55 | 240 | Cal. Obt. | 55.96 55.84 | 6.39 6.36 | 7.83 7.66 |

TABLE I-continued $$Ar-X-N\underset{}{\bigcirc}N-CH_2-A \quad (I)$$

| Code Number | Ar— | —X— | A— | Form | Empirical Formula | Molecular weight | Melting point (°C.) | ELEMENTARY ANALYSIS % | | C | H | N |
|---|---|---|---|---|---|---|---|---|---|---|---|---|
| 84 | CH₃O, CH₃O, CH₃O (trimethoxyphenyl) | —CH=CH—CO— (trans) | " | HCl | $C_{23}H_{34}ClN_3O_5$ | 467.98 | 190 | Cal. | Obt. | 59.03 / 59.22 | 7.32 / 7.51 | 8.98 / 9.01 |
| 85 | benzodioxin | —CH=CH—CO— (trans) | " | " | $C_{22}H_{30}ClN_3O_4$ | 435.94 | ≃200 (decomposition) | Cal. | Obt. | 60.61 / 60.60 | 6.94 / 7.10 | 9.64 / 9.49 |
| 86 | 4-CH₃-phenyl | —CH=CH—CO— (trans) | " | " | $C_{21}H_{30}ClN_3O_2$ | 391.93 | 220 | Cal. | Obt. | 64.35 / 64.33 | 7.72 / 7.73 | 10.72 / 10.99 |
| 87 | 4-CF₃-phenyl | —CH=CH—CO— (trans) | " | " | $C_{21}H_{27}ClF_3N_3O_2$ | 445.91 | >200 (decomposition) | Cal. | Obt. | 56.56 / 56.76 | 6.10 / 5.86 | 9.42 / 9.50 |
| 88 | 3,4-diCl-phenyl | —CH=CH—CO— (trans) | " | Base | $C_{20}H_{25}Cl_2N_3O_2$ | 410.34 | 153 | Cal. | Obt. | 58.54 / 58.40 | 6.14 / 6.05 | 10.24 / 10.01 |
| 89 | CH₃O, CH₃O, CH₃O (3,4,5-trimethoxyphenyl) | —CH=CH—CO— (trans) | —CON⟨ (tropane) | " | $C_{25}H_{35}N_3O_5$ | 457.55 | 175 | NMR spectrum (CDCl₃) δ ppm: 6.68 and 7.5, d(J=15Hz): CH=CH trans; 6.65,s: 2 aromatic Hs; 4,4,m: 2 tropanic protons in positions 1 and 5; 3.82, s: 3CH₃O; 3.65,m: 4 piperazinic Hs; 3.10,s: ⟩N—CH₂—CO—; 2.5,m: 4 piperazinic Hs;1.6,m:10 tropanic Hs | | | |

The derivatives of formula (I) and the salts and hydrates thereof were tested on laboratory animals and revealed pharmacological activities and especially activities stimulating, protecting and/or correcting cerebral functions.

These activities were shown, more particularly by the mnesic retention test of exploratory activity effected according to the following method:

In an APELAB ACTIMETER [BOISSIER and SIMON, Arch. Inter. Pharmacodyn. 158, 212, (1965)], the exploratory activity during 5 mn of male SWISS-WEBSTER mice is measured, then the animals receive an intraperitoneal (or an oral injection dose), of the compounds of formula (I) or the salts thereof or of physiological serum. After a week, the exploratory activity of the treated animals is again measured by an habituation, that is by a statistically significant decrease (t of STUDENT by mated groups) of the exploratory activity.

To illustrate the invention, we give in Table II below, the results obtained with some compounds of the invention.

The approximate acute toxicity is determined according to the method described by MILLER and TAINTER in Proc. Soc. Exp. Biol. Med. 57, 261 (1944).

The results obtained with some compounds of the invention are also given, by way of examples in this table II.

TABLE II

| Compound tested Code number | Mnesic test | | Acute toxicity | |
|---|---|---|---|---|
| | Dose (mice) (mg/kg/i.V.) | % reduction of the exploratory activity | Dose (mice) (mg/kg/i.v.) | % mortality |
| 2 | 1 | 14.7 | — | |
| 8 | 3 | 17.5 | — | |
| 11 | 3 | 28.4 | 200 i.v. | 0 |
| 12 | 10 | 14.4 | — | |
| 23 | 3 | 18.4 | 200 i.v. | 0 |
| 26 | 10 | 14.3 | — | |
| 29 | 3 | 9.9 | 200 i.v. | 0 |
| 36 | 10 | 18.4 | 200 i.v. | 0 |
| 37 | 1 | 25.2 | 400 i.p. | 0 |
| 38 | 3 | 28.6 | 200 i.v. | 10 |
| 40 | 3 | 28.9 | 120 i.v. | 50 |
| 43 | 10 | 23.8 | — | |
| 44 | 3 | 24.0 | 200 i.v. | 0 |
| 47 | 1 | 26.5 | 200 i.v. | 0 |
| 48 | 30 | 26.1 | 200 i.v. | 0 |
| 49 | 1 | 15.7 | 205 i.v. | 50 |
| 55 | 3 | 18.7 | — | |
| 56 | 3 | 23.5 | — | |

As the above results show, the compounds of the invention present marked pharmacological activities and low toxicity. These compounds find then an application in therapeutics. Thus, they will be more particularly used for stimulating intellectual efficiency in normal subjects, for preserving the cerebral functions in aged subjects and for treating trouble of vigilance and/or memorization consequent on different pathologies, particularly brain traumatisms, cerebral disturbances or acute or sub-acute cerebro-vascular accidents.

The present invention further extend to pharmaceutical compositions containing as active ingredient, one at least of the derivatives of formula (I) or by the salts or hydrates thereof, these compositions being able to be formulated more especially with a view to their oral or parenteral administration. Thus, they may be administered orally in the form of pills, capsules or tablets, or in the form of drinkable solutions, in an amount up to 2.5 g/day, to be taken in several doses per day (up to six doses) or parenterally in the form of injectable ampoules containing up to 1 g of active ingredient (1 to 3 injections per day).

In the case of the oral administration in the form of pills, capsules or tablets, the latter advantageously comprise a vehicle (such as cellulosic derivatives, vinylic polymers or gums for example) allowing modulation of drug release. The drinkable solutions are preferably aqueous solutions or suspensions (vehicle=water) or partially aqueous solutions or suspensions (vehicle=water+alcohol, water+glycerine or water+propylene glycol). In the case of the parenteral administration, the active ingredient may be injected in the form of suspensions or solutions of freeze drying products containing said active ingredient.

We claim:

1. New compounds having the general formula:

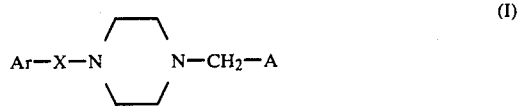

in which X represents:
either the chain of trans configuration

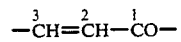

or the chain

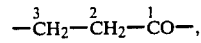

connected to Ar by their carbon atom 3, in which case A represents:
a carbohydroxamic (—CONHOH), Ar then representing the (3,4,5-trimethoxy)phenyl nucleus,
a carboxyl group (COOH), Ar then representing the parachlorophenyl, para-hyroxyphenyl, (3,4-methylenedioxy)phenyl or (3,5-dimethoxy 4-hydroxy)phenyl nucleus, or
an amido group of structure CO—NR$_2$R$_3$ in which the pair (R$_2$, R$_3$) takes on one of the following meanings: (H,H), (C$_1$-C$_4$ alkyl, C$_1$-C$_4$ alkyl), (H, C$_3$-C$_6$ cycloalkyl), (H, C$_3$-C$_6$ cycloalkylmethyl), (H, phenyl), (H, phenyl substituted by one or more halogen atoms), (H, phenyl substituted by one or more methyl or methoxy groups), (H, benzyl), (H, benzyl substituted by one or more halogen atoms), (H, benzyl substituted by one or more methyl or methoxy groups), (CH$_3$, benzyl), (CH$_3$, benzyl substituted by one or more halogen atoms), (CH$_3$, benzyl substituted by one or more methyl or methoxy groups), (H, allyl), (H, propargyl), R$_2$, R$_3$ being also able to form jointly with the nitrogen atom to which they are linked, a pyrrolidino, piperidino, or morpholino radical; Ar then representing a phenyl nucleus, a phenyl nucleus substituted by one or more halogen atoms, by one or more methoxy groups, by a methyl group, by a trifluoromethyl group or by one or two hydroxy radicals, a 1,3-benzodioxolyl group:

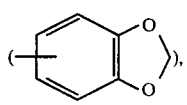

a 1,4-benzodioxannyl group:

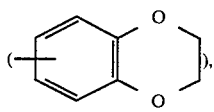

a (5-methoxy) 1,4-benzodioxannyl group:

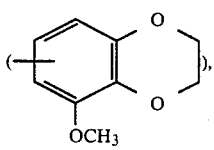

a naphthyl group, the (3-methoxy 4-hydroxy)phenyl group, the (3-hydroxy 4-methoxy)phenyl group, the (3,5-dimethoxy 4-hydroxy)phenyl group or a (4-$C_2$-$C_4$ alkoxy 3,5-dimethoxy)phenyl group;

A not however being able to assume the following values: $CONH_2$, $CON(C_1$-$C_4$ alkyl$)_2$,

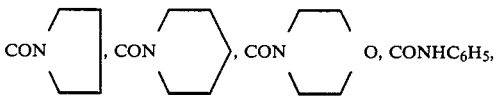

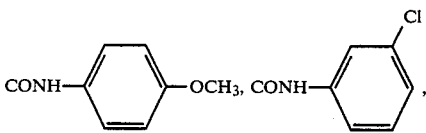

when Ar represents the (3,4,5-trimethoxy)phenyl group; A not however being able to assume the following values: $CONH_2$, $CON(C_1$-$C_4$ alkyl$)_2$,

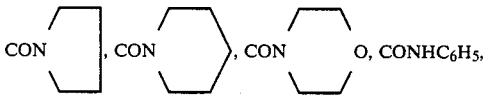

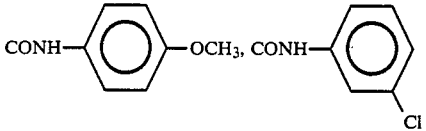

when Ar represents the (3,5-dimethoxy 4-hydroxy)phenyl group and A not however being able to assume the value $CON(C_2H_5)_2$ when Ar=2-hydroxyphenyl and X=$CH_2$—$CH_2CO$;
or an N-isopropylcarboxamido, Ar then representing a (3-methoxy 4-hydroxy)phenyl nucleus;
or the chain of trans configuration

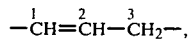

linked to Ar by its carbon atom 1 or the chain —$CH_2$—$CH_2$—$CH_2$—, in which case A represents a carboxamido, N-isopropylcarboxamido, pyrrolidinocarbonyl or piperidinocarbonyl group, Ar then representing a (3,4,5-trimethoxy)phenyl or (3,4-methylenedioxy)phenyl group, with the proviso that A cannot represent a pyrrolidinocarbonyl group when Ar=(3,4,5-trimethoxy)phenyl, as well as the acid addition salts thereof and the hydrates of these derivatives and salts.

2. The compounds as claimed in claim 1, wherein X represents the

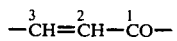

chain of trans configuration, A represents the carboxyl group and Ar takes on any one of the following values:

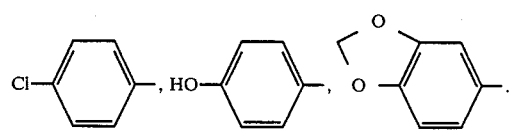

3. A compound as defined in claim 1 where X represents —CH=CH—CO— in the trans configuration.

4. A compound as defined in claim 3 wherein A represents

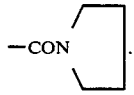

5. A compound as defined in claim 3, wherein A represents

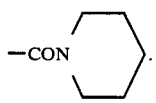

6. A compound as defined in claim 4 wherein Ar represents

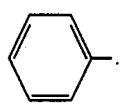

7. A compound as defined in claim 4 wherein Ar represents

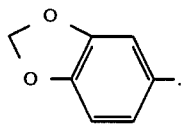

8. A compound as defined in claim 4 wherein Ar represents

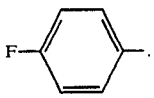

9. A compound as defined in claim 4 wherein Ar represents

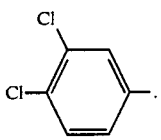

10. A compound as defined in claim 4 wherein Ar represents

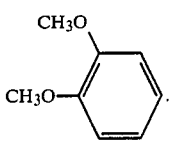

11. A compound as defined in claim 4 wherein Ar represents

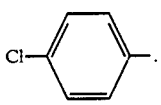

12. A compound as defined in claim 4 wherein Ar represents

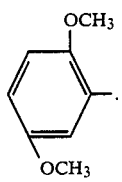

13. A compound as defined in claim 5 wherein Ar represents

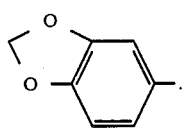

14. A compound as defined in claim 5 wherein Ar represents

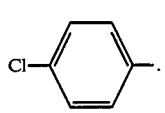

15. A compound as defined in claim 5 wherein Ar represents

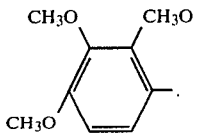

16. A compound as defined in claim 1, wherein X represents the

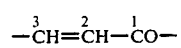

chain of trans configuration, A is $CONH_2$, and Ar is the (3,4-methylenedioxy)phenyl group.

17. A compound as defined in claim 1, wherein X represents the

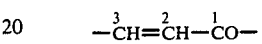

chain of trans configuration, A is

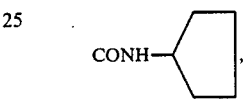

and Ar is (3,4,5-trimethoxy)phenyl.

18. A compound as defined in claim 1, wherein X represents the

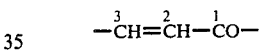

chain of trans configuration, A is the N-isopropylcarboxamide group and Ar is (3-methoxy 4-hydroxy)phenyl.

19. A compound as defined in claim 1, wherein X represents the

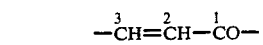

chain of trans configuration, A is N-(3,4,5,-trimethoxy)-benzylcarboxamide and Ar is (3,4,5-trimethoxy)phenyl.

20. A pharmaceutical composition for stimulating, protecting and/or correcting the cerebral functions comprising a therapeutically effective amount of a compound having the general formula:

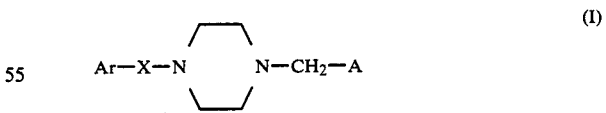 (I)

in which X represents:
either the chain of trans configuration

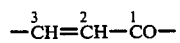

or the chain

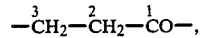

connected to Ar by their carbon atom 3, in which case A represents:

a carbohydroxamic (—CONHOH), Ar then representing the (3,4,5-trimethoxy)phenyl nucleus, a carboxyl group (COOH), Ar then representing the parachlorophenyl, para-hydroxyphenyl, (3,4-methylenedioxy)phenyl or (3,5-dimethoxy 4-hydroxy)phenyl nucleus, or an amido group of structure CO—NR$_2$R$_3$ in which the pair (R$_2$, R$_3$) takes on one of the following meanings: (H,H), (C$_1$-C$_4$ alkyl, C$_1$-C$_4$ alkyl), (H, C$_3$-C$_6$ cycloalkyl), (H, C$_3$-C$_6$ cycloalkylmethyl), (H, phenyl), (H, phenyl substituted by one or more halogen atoms), (H, phenyl substituted by one or more methyl or methoxy groups), (H, benzyl), (H, benzyl substituted by one or more halogen atoms), (H, benzyl substituted by one or more methyl or methoxy groups), (CH$_3$, benzyl), (CH$_3$, benzyl substituted by one or more halogen atoms), (CH$_3$, benzyl substituted by one or more methyl or methoxy groups), (H, allyl), (H, propargyl), R$_2$, R$_3$ being also able to form jointly with the nitrogen atom to which they are linked, a pyrrolidino, piperidino, or morpholino radical; Ar then representing a phenyl nucleus, a phenyl nucleus substituted by one or more halogen atoms, by one or more methoxy groups, by a methyl group, by a trifluoromethyl group or by one or two hydroxy radicals, a 1,3-benzodioxolyl group:

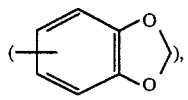, a 1,4-benzodioxannyl group:

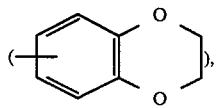, a (5-methoxy) 1,4-benzodioxannyl group:

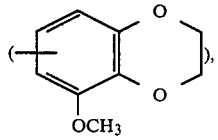

a naphthyl group, the (3-methoxy 4-hydroxy)phenyl group, the (3-hydroxy 4-methoxy)phenyl group, the (3,5-dimethoxy 4-hydroxy)phenyl group or a (4—C$_2$-C$_4$ alkoxy 3,5-dimethoxy)phenyl group;

A not however being able to assume the following values: CONH$_2$, CON(C$_1$-C$_4$ alkyl)$_2$,

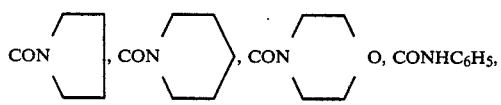

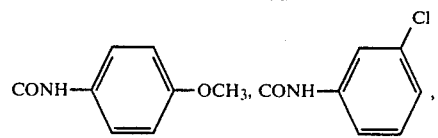

when Ar represents the (3,4,5-trimethoxy)phenyl group; A not however being able to assume the following values: CONH$_2$, CON(C$_1$-C$_4$ alkyl)$_2$,

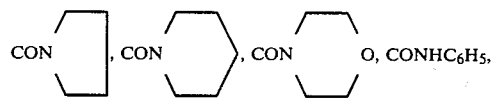

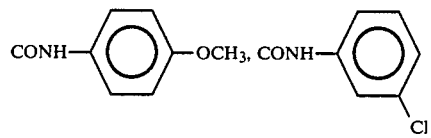

when Ar represents the (3,5-dimethoxy 4-hydroxy)phenyl group and

A not however being able to assume the value CON(C$_2$H$_5$)$_2$ when Ar=2-hydroxyphenyl and X=CH$_2$—CH$_2$CO;

or an N-isopropylcarboxamido, Ar then representing a (3-methoxy 4-hydroxy)phenyl nucleus;

or the chain of trans configuration

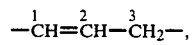, linked to Ar by its carbon atom 1 or the chain —CH$_2$—CH$_2$—CH$_2$—, in which case A represents a carboxamido, N-isopropylcarboxamido, pyrrolidinocarbonyl or piperidinocarbonyl group, Ar then representing a (3,4,5-trimethoxy)phenyl or (3,4-methylenedioxy)phenyl group, with the proviso that A cannot represent a pyrrolidinocarbonyl group when Ar=(3,4,5-trimethoxy)phenyl, as well as the acid addition salts thereof and the hydrates of these derivatives and salts, in combination with a pharmacologically acceptable vehicle.

21. A method of stimulating, protecting and/or correcting the cerebral functions in a human being, which comprises administering internally to a human being requiring such treatment, a therapeutically effective amount of a compound having the general formula:

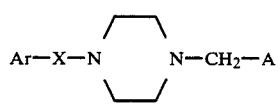 (I)

in which X represents:
either the chain of trans configuration

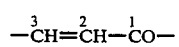

or the chain

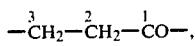

connected to Ar by their carbon atom 3, in which case A represents:

a carbohydroxamic (—CONHOH), Ar then representing the (3,4,5-trimethoxy)phenyl nucleus, an ethoxycarbonyl (COOEt) group, Ar then representing the (2,3,4-trimethoxy)phenyl or (2,4,6-trimethoxy)phenyl nucleus, a carboxyl group (COOH), Ar then representing the parachlorophenyl, para-hydroxyphenyl, (3,4-methylenedioxy)phenyl or (3,5-dimethoxy 4-hydroxy)phenyl nucleus, or an amido group of structure CO—NR$_2$R$_3$ in which the pair (R$_2$, R$_3$) takes on one of the following meanings: (H,H), (H, C$_1$-C$_4$ alkyl) (C$_1$-C$_4$ alkyl, C$_1$-C$_4$ alkyl), (H, C$_3$-C$_6$ cycloalkyl), (H, C$_3$-C$_6$ cycloalkylmethyl), (H, phenyl), (H, phenyl substituted by one or more halogen atoms), (H, phenyl substituted by one or more methyl or methoxy groups), (H, benzyl), (H, benzyl substituted by one or more halogen atoms), (H, benzyl substituted by one or more methyl or methoxy groups), (CH$_3$, benzyl), (CH$_3$, benzyl substituted by one or more halogen atoms), (CH$_3$, benzyl substituted by one or more methyl or methoxy groups), (H, allyl), (H, propargyl), R$_2$, R$_3$ being also able to form jointly with the nitrogen atom to which they are linked, a pyrrolidino, piperidino, or morpholino radical; Ar then representing a phenyl nucleus, a phenyl nucleus substituted by one or more halogen atoms, by one or more methoxy groups, by a methyl group, by a trifluoromethyl group or by one or two hydroxy radicals, a 1,3-benzodioxolyl group:

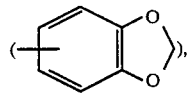

a 1,4-benzodioxannyl group:

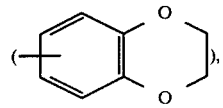

a (5-methoxy) 1,4-benzodioxannyl group:

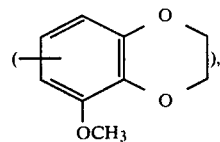

a naphthyl group, the (3-methoxy 4-hydroxy)phenyl group, the (3-hydroxy 4-methoxy)phenyl group, the (3,5-dimethoxy 4-hydroxy)phenyl group or a (4-C$_2$-C$_4$ alkoxy 3,5-dimethoxy)phenyl group;

A not however being able to assume the following values: CONHCH$_3$, CONH$_2$, CONHC$_2$H$_5$, CONHC$_3$H$_7$n, CONHC$_3$H$_7$iso, CON(CH$_3$)$_2$, CON(C$_2$H$_5$)$_2$, CON(C$_3$H$_7$n)$_2$, CON(C$_3$H$_7$iso)$_2$,

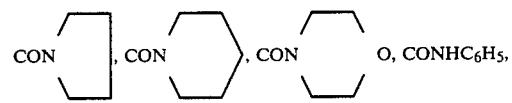

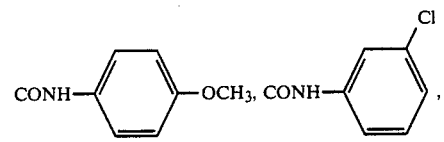

when Ar represents the (3,4,5-trimethoxy)phenyl or (3,5-dimethoxy 4-hydroxy)phenyl group; and the value CON(C$_2$H$_5$)$_2$ when Ar=2-hydroxy phenyl and X=CH$_2$CH$_2$CO, or the chain of trans configuration

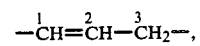

linked to Ar by its carbon atom 1 or the chain —CH$_2$—CH$_2$—CH$_2$—, in which case A represents a carboxamido, N-isopropylcarboxamido, pyrolidinocarbonyl or piperidinocarbonyl group, Ar then representing a (3,4,5-trimethoxy)phenyl or (3,4-methylenedioxy)phenyl group, with the proviso that A cannot represent a pyrrolidinocarbonyl group with Ar=(3,4,5-trimethoxy)phenyl, as well as the acid addition salts thereof and the hydrages of these derivatives and salts.

* * * * *